United States Patent [19]
Geus et al.

[11] Patent Number: 5,986,110
[45] Date of Patent: Nov. 16, 1999

[54] PROCESS FOR THE SELECTIVE OXIDATION OF HYDROCARBONS

[75] Inventors: John Wilhelm Geus, Bilthoven; Rudolf Alfred Overbeck, Utrecht, both of Netherlands

[73] Assignee: Engelhard De Meern B. V., De Meern, Netherlands

[21] Appl. No.: 08/824,506

[22] Filed: Mar. 26, 1997

Related U.S. Application Data

[62] Division of application No. 08/234,657, Apr. 28, 1994, Pat. No. 5,707,917.

[30] Foreign Application Priority Data

Apr. 29, 1993 [NL] Netherlands ............... 9300737

[51] Int. Cl.$^6$ ................................ C07D 307/60
[52] U.S. Cl. .................. 549/259; 549/248; 549/249; 549/475
[58] Field of Search ............................ 549/259

[56] References Cited

U.S. PATENT DOCUMENTS

| | | | |
|---|---|---|---|
| 3,156,707 | 11/1964 | Kerr | 549/259 |
| 3,867,411 | 2/1975 | Raffelson et al. | 549/260 |
| 4,261,899 | 4/1981 | Gelbein | 260/346.4 |
| 4,510,258 | 4/1985 | Suciu et al. | 549/209 |
| 4,594,433 | 6/1986 | Suciu et al. | 549/256 |
| 4,668,802 | 5/1987 | Contractor | 549/259 |
| 4,740,360 | 4/1988 | Geus et al. | 423/55 |
| 4,869,792 | 9/1989 | Geus et al. | 204/96 |

FOREIGN PATENT DOCUMENTS

| | | |
|---|---|---|
| 0189621 | 8/1986 | European Pat. Off. |
| 1190451 | 4/1965 | Germany |
| 2145010 | 3/1985 | United Kingdom |

OTHER PUBLICATIONS

Brinen, J.S. et al., X–Ray Photoelectron Spectroscopy Studies of the Rhodium on Charcoal Catalyst, *Journal of Catalysis* 40, 295–300 (1975).
Cavani et. al., Applied Catalysis, vol. 15, pp. 151–160, 1985.
Busca et. al., "Surface Dynamics of Adsorbed Species on Heterogeneous Oxidation Catalysts etc.", J. Am. Chem. Soc. vol. 111, pp. 46–54, 1989.

*Primary Examiner*—Bernard Dentz
*Attorney, Agent, or Firm*—Weingarten, Schurgin, Gagnebin & Hayes LLP

[57] ABSTRACT

The invention relates to a heterogeneous vanadium-phosphorus oxide catalyst system for the selective oxidation of hydrocarbons, which may or may not be saturated, comprising a support based on one or more metal oxides, and vanadium-phosphorus oxide in an amount of from 0.01 to 45 wt. %, based on the weight of the catalyst and calculated as $(VO)_2P_2O_7$, to a process for the selective oxidation of an organic compound in the presence of a vanadium-phosphorus oxide catalyst, which process comprises an oxidation and a reduction phase, wherein a hydrocarbon is contacted with said catalyst in the reduction phase and in oxidized or non-oxidized form is adsorbed to the catalyst, whereafter the thus loaded catalyst is brought into the oxidation phase, the desired product is formed in the presence of gaseous oxygen and subsequently separated.

11 Claims, 3 Drawing Sheets

PROCESS FOR THE SELECTIVE OXIDATION OF HYDROCARBONS

This application is a division of application Ser. No. 08/234,657, filed Apr. 28, 1994 now U.S. Pat. No. 5,707,917.

FIELD AND BACKGROUND OF THE INVENTION

This invention relates to a catalyst for the selective oxidation of hydrocarbons, which may or may not be saturated, to oxygen-containing organic compounds. More particularly, the invention relates to a catalyst for the selective oxidation of hydrocarbons to oxygen-containing compounds, such as the oxidation of n-butane to maleic acid anhydride. The invention further relates to a process for the selective oxidation of hydrocarbons, which may or may not be saturated, to oxygen-containing organic compounds. Finally, the invention also relates to the preparation of such a catalyst.

According to the prior art, n-butane is oxidized to maleic acid anhydride with a good selectivity in the presence of catalysts containing vanadium oxide and phosphate. Suitable catalysts can be prepared in two different manners. In both cases, the starting material is vanadium(V), whereafter the vanadium(V) is reduced to vanadium(IV), whereafter phosphate is added. According to the first method, hydrochloric acid is added to the solution of vanadium(V), whereafter at elevated temperature the vanadium is reduced with hydrogen chloride to form chlorine. According to the second method, work is done in an organic solvent, such as for instance i-butanol. At elevated temperature the organic solvent reduces the dissolved vanadium(V) which is subsequently stabilized by reaction with the dissolved phosphate.

In general the selective oxidation is carried out with an excess of oxygen. To prevent the formation of explosive mixtures, generally a content of 1.5 vol. % n-butane in air is worked with. Typical is a conversion of about 90% of the n-butane present in the feed, which is converted to maleic acid anhydride with a selectivity of about 60%. To realize such a conversion, the temperature of the catalyst bed must be maintained at about 400° C. Naturally, with such an exothermic reaction the temperature in the catalyst bed will increase; generally, a higher final temperature leads to a poorer selectivity with a higher conversion. About 50% of the n-butane supplied then becomes available as maleic acid anhydride with the current technical implementation of the process.

Customarily, the oxidation reaction over the vanadium, phosphorus and oxygen-containing catalysts is carried out by passing the reactants through the reactor once, a so-called 'once through' process. One of the most important limitations of this process, which uses a fixed catalyst bed, is that only an n-butane concentration of 2 vol. % at most can be used; higher n-butane contents may lead to explosions.

To increase the yield of maleic acid anhydride, recently other embodiments of the process have been proposed. One of the successful newly proposed embodiments is a fluidized bed reactor. It is then possible, without danger of explosions, to increase the concentration of the n-butane in the feed to substantially the stoichiometric value. As a result, the productivity per unit volume of the reactor increases, which leads to lower investment costs. (GB-A 2,145,010).

A fluidized bed reactor has still other advantages, viz. a markedly improved dissipation of the reaction heat, so that areas having locally a high temperature are effectively avoided. Although a fluidized bed process is economically and technically attractive, the selectivity of the catalytic oxidation is lower at higher n-butane concentrations, while moreover a (highly) wear-resistant catalyst must be used. In particular in the case of vanadium-phosphate-oxygen catalysts, the production of a wear-resistant catalyst is a difficult task.

It is known from EP-A 189,621 that the efficiency of the conversion to maleic acid anhydride can be increased by employing two separate reaction steps. The two reaction steps are carried out in separate reactors or in separate sections of a single reactor. In this case, n-butane, preferably in the absence of molecular oxygen, is contacted with the oxidized catalyst. After reaction with the lattice-oxygen present in the catalyst, whereby maleic acid anhydride is formed with a good selectivity, the residual butane and the product formed are removed, and the catalyst is passed into a reoxidation zone, where the catalyst is reoxidized with air oxygen.

Since the reduction and the oxidation of the catalyst take place in separate reactors, a more concentrated n-butane stream can be used. Moreover, in such a circulating fluidized bed, the heat transfer proceeds faster than in a fixed catalyst bed, so that the temperature is better controllable. Selectivity of up to 90% has been reported for the use of this process with two separate catalytic reactors. Although the yield of maleic acid anhydride is markedly increased, the catalyst developed for this process has two shortcomings. Because the conventional vanadium-phosphorus-oxygen catalyst is not wear-resistant, a new catalyst had to be developed, whose individual catalyst bodies are covered with a porous layer of silicon dioxide. On the one hand, this porous layer reduces wear, but, on the other hand, the inert porous layer limits the transport of reactants and reaction products. Moreover, the surface/volume ratio of the vanadium-phosphorus-oxygen constituent in the newly developed catalyst is relatively low, as in the conventional catalysts. To obtain a useful conversion of n-butane, large quantities of catalyst have to be recirculated per kilogram of maleic acid anhydride. In the literature it has been published that per kilogram of catalyst only about 2 g maleic acid anhydride is obtained.

It appears from the above-described prior art that there is a great need for a better catalyst in order to overcome the drawbacks of the current vanadium-phosphorus-oxygen. In general, wear-resistant catalysts in which the catalytically active component has a high surface area to volume ratio are obtained by providing the active component on a so-called support. Such a support is a highly porous, thermostable material, on the surface of which the active component or components are provided in more or less finely divided form. Commercially, a wide variety of preformed support bodies are available; it is therefore easy to select a suitable support with the necessary wear-resistance and a desired pore distribution. If the active component or components are provided on a support selected on the basis of the process in which the catalyst is to function, a catalyst meeting often conflicting requirements is readily obtained.

In spite of the fact that the vanadium-phosphorus-oxygen has already been employed on a technical scale for over a decade and in spite of the fact that the shortcomings of the current catalyst have been suitably recognized, efforts to prepare a satisfactory supported vanadium-phosphorus-oxygen catalyst have been unsuccessful to date. The selectivity of the supported vanadium-phosphorus-oxygen catalysts prepared heretofore was invariably found to be unacceptably low.

This is the reason that alternatives have been searched for. The first possibility has already been mentioned above, viz. the provision of a porous layer of wear-resistant silicon dioxide on porous particles of the vanadium-phosphorus-oxygen catalyst. Another method of preparing an improved catalyst is described in the above-mentioned GB-A 2,145, 010. There a mixture of the oxides of vanadium and phosphorus is treated with an acid, preferably phosphoric acid or hydrochloric acid, the material thus obtained is mixed with zirconium dioxide or titanium dioxide, and the suspension obtained is subsequently spray-dried. Wear-resistant bodies of dimensions of from 3 to 10 $\mu$m are then obtained. It will be clear that neither of the methods leads to catalysts where the active component is provided on (highly) porous support bodies in finely divided form.

An important disadvantage of the known catalysts based on vanadium, phosphorus and oxygen (VPO) is, moreover, the requirement that the catalysts must possess a specific structure to obtain the desired activity and selectivity.

A first object of the present invention is to provide a suitable catalyst for the selective oxidation of hydrocarbons, which catalyst is less dependent on the structure of the active component and which moreover requires no special measures for increasing its usefulness in various more modern oxidation processes.

SUMMARY OF THE INVENTION

Surprisingly, it has now been found that the provision of (hydrated) vanadium(III) oxide on a suitable support, either simultaneously with phosphate or followed by reaction of the hydrated vanadium(III) oxide provided on the support with phosphate leads to catalysts which exhibit excellent properties for the oxidation of hydrocarbons. It is known that on non-alkaline support materials, such as silicon dioxide, hydrated vanadium(III) oxide can be provided in extremely finely divided form, preferably by deposition-precipitation. On aluminum oxide and titanium dioxide, too, vanadium (III) oxide can in this way be applied as extremely small particles with a homogeneous distribution over the surface of the support. Surprisingly, in the reaction with phosphates or with phosphoric acid a catalyst is formed which yields an eminent activity and selectivity.

The invention primarily relates to a heterogeneous vanadium-phosphorus oxide catalyst system for the selective oxidation of hydrocarbons, which may or may not be saturated, comprising a support based on one or more metal oxides, and vanadium-phosphorus oxide in an amount of from 0.01 to 45 wt. %, based on the weight of the catalyst and calculated as $(VO)_2P_2O_7$.

It has been found that such a catalyst on support, where the amount of support is at least 55 wt. % and more particularly more than 60 wt. %, and where the VPO component has been applied to the surface of the support, can be readily used in a variety of selective oxidation processes, exhibits hardly any wear, if at all, and requires no specific structure of the VPO component. More particularly, it has been found that no limitations with regard to transport arise in the catalyst system.

BREIF DESCRIPTION OF THE DRAWINGS

DETAILED DESCRIPTION OF THE PREFERRED EMBODIMENT

Figure 1:
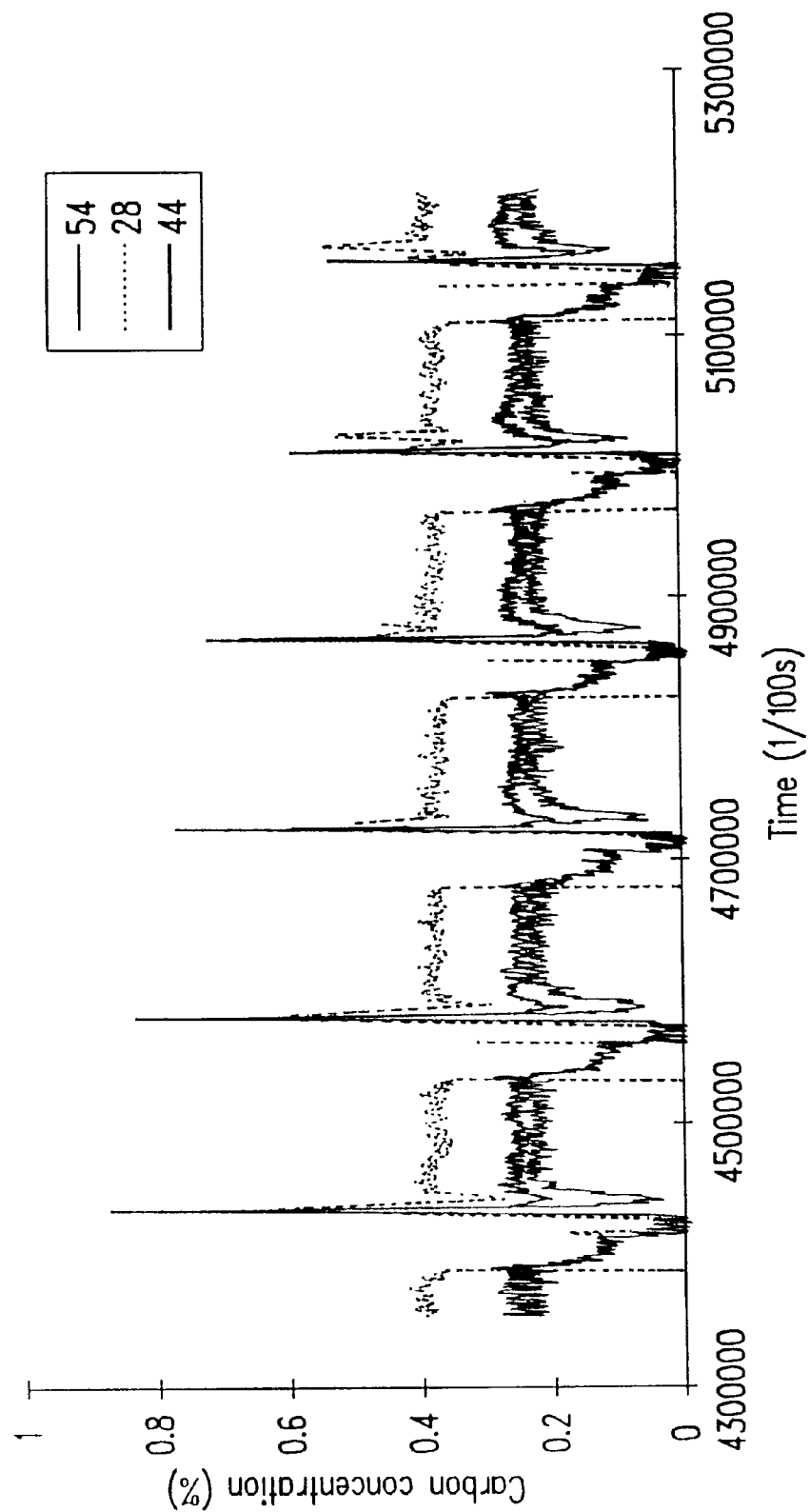
FIG. 1 is a graph of carbon concentration versus time useful in explaining the invention.

According to a preferred embodiment of the invention, the VPO component is well dispersed over the surface of the support.

With the catalysts according to the invention, it is of importance that the surface of the support is occupied with the finely divided active component or components as uniformly as possible. The best way of determining the occupation of the surface of a support with active component is X-ray photoelectron spectroscopy (XPS). With this technique the chemical composition of the surface layer of the catalysts can be determined. The ratio of the intensities of a type of atoms forming part of the support and of vanadium is representative of the extent to which the surface of the support is covered with active component. If we take a titanium oxide support as an example, then the ratio of the intensities of titanium and vanadium in the X-ray photoelectron spectrum of the catalyst is a measure for the occupation of the support surface with the active component. In the case of a high ratio, the surface is poorly covered by the vanadium, whilst in the case of a lower ratio, the surface of the titanium dioxide support is homogeneously occupied with small particles. Naturally, the load of the support also plays a role. In the case of a low load of the support, a high ratio in the X-ray photoelectron spectrum will be measured sooner than in the case of a high load.

It has been now found that the product of the ratio of the intensities of a type of atom of the support and vanadium in the X-ray photoelectron spectrum and the load expressed in the load in percent by weight is a good indication of the extent of dispersal. In practice this means that the dispersion number, the measure for the dispersal, has a value between 0.01 and 500, more particularly between 0.01 and 300. The dispersion number is defined as the product of the percentage by weight of VPO, calculated as $(VO)_2P_2O_7$ on the catalyst, and the atomic ratio of metal of the support component, in this connection understood to include silicon, to vanadium determined with XPS. XPS is described inter alia in the article of Brinen et al, X-Ray Photoelectron spectroscopy studies of the rhodium on charcoal catalyst, J. of Catalysis, 40, 295–300 (1975), using a correction for the background according to Shirley, D. A. Shirley, Phys.Rev.B, 1972, 5, 4709.

Because the amount of support in the catalyst is of great significance, catalysts according to the invention contain an amount of support material constituting a minimum of 55% and preferably a maximum of 95% of the weight. The use of a suitable support is of importance because the support is generally cheaper than the vanadium. In addition, the wear-resistance of the catalyst is higher in the case of a high support material content. Other advantages of providing the active component(s) on a suitable support are the fact that the specific surface and the pore distribution of the support can be selected, so that impediments to transport can be prevented. In addition, it has been found, surprisingly, that if particular support materials, such as titanium dioxide, are used, the catalytic properties of the active component are modified. The extent to which the catalytic properties are affected depends on the load; a lower load leads to a stronger effect of the support on the catalytic properties. In this way, the catalytic properties of the catalyst can be controlled as well.

The catalyst according to the invention preferably contains, as support, one or more metal oxides, in this connection understood to include, by preference, titanium oxide, zirconium oxide, silicon dioxide, aluminum oxide or combinations thereof. The content of support is preferably at least 75 wt. %, since such a content already yields good results.

An important advantage of the catalyst according to the invention is that it is already active at lower temperatures. With the present catalyst, temperatures lower than 360° C. suffice.

The invention also relates to a process for the selective oxidation of hydrocarbons, using such a catalyst. More particularly, the invention further relates to a process for the selective oxidation of hydrocarbons of the above-described type, where the catalyst is passed through oxidation and reduction zones, in which process the present catalyst can be suitably used.

It has now been found that the above-mentioned process in which the catalyst is recirculated from a zone where the catalyst reacts with the organic compound to a zone where the catalyst is reoxidized, can be considerably improved. In accordance with the improved process, the catalyst is also recirculated between an oxidation and a reduction zone, but the catalyst, before it is passed into the reoxidation zone, is allowed to remain loaded with adsorbed, partially oxidized saturated hydrocarbon, whereafter the thus adsorbed hydrocarbon, after transfer, is allowed to react in the second reaction zone with gaseous oxygen or with other compounds to form oxygen-containing products.

The invention accordingly relates to a process for the selective oxidation of an organic compound in the presence of a vanadium-phosphorus oxide catalyst, which process comprises an oxidation and a reduction phase, wherein a hydrocarbon is contacted with said catalyst in the reduction phase and in oxidized or non-oxidized form is adsorbed to the catalyst, whereafter the thus loaded catalyst is brought into the oxidation phase, the desired product is formed in the presence of gaseous oxygen and is subsequently separated.

According to the invention it is possible to use a fixed catalyst bed and to pass alternately (air) oxygen and a saturated hydrocarbon through this bed. Selective oxidations which can be carried out in accordance with the present invention are the oxidation of $C_4$ hydrocarbons to form the various oxidized variants thereof, such as butene, butadiene, crotonic aldehyde, 2,5-dihydrofuran, maleic acid, tetrahydrofuran and maleic acid anhydride. Oxidation of pentane yields inter alia phthalic acid anhydride. Preferably, the process according to the invention is carried out with n-butane, the reaction product being maleic acid anhydride.

To enable the partial oxidation of the saturated hydrocarbon or the n-butane to adsorbed reactive species, the saturated hydrocarbon or the n-butane should preferably be contacted with the catalyst at a relatively low temperature. At such a low temperature, which is preferably between 200 and 500° C., then only a very minor amount of butane per unit weight of the catalyst reacts. It is observed that in this connection it is possible to work the reduction phase and the oxidation phase at different temperatures.

When using the catalyst according to the present invention, a temperature of less than 360° C. can be employed in the reduction phase, whilst the oxidation phase can be worked at temperatures below 300° C.

In general, the process according to the invention can be carried out in a number of ways. In the first place, it is possible to work the reduction phase in the absence of oxygen or in the presence of a minor proportion of oxygen with regard to the hydrocarbon. The oxidation phase can be carried out in the absence of hydrocarbon or in the presence of an amount of hydrocarbon which is present in a minor proportion with regard to the amount of oxygen. This can be realized by appropriately feeding oxygen and hydrocarbon to the reactor or reactors. An important variant of the process according to the invention is formed by the supply of a relative minor proportion of hydrocarbon to the oxidation zone. In this way a considerable increase of the yield of oxidation product is obtained. Apart from the yield of the oxidation of the hydrocarbon in the reduction zone using the oxygen bound to the catalyst, a second product stream is obtained in this way. As a mirror image of this variant, a minor proportion of oxygen can be fed to the reduction zone. Thus, already in the reduction zone the desired oxidation product is formed, which can be removed from the reduction zone.

In the practice of the process according to the invention, the hydrocarbon can be supplied in undiluted form, but it is also possible to dilute it with an inert gas. Non-absorbed hydrocarbon, if any, is removed from the reduction zone and recirculated after treatment, if any. Preferably used as oxidizing component is molecular oxygen, either in the form of air or in more purified form. Although this is not preferred, it is also possible to use other oxidizing components, which have an effect comparable to oxygen.

It is noted that in the practice of the process according to the invention at least a part of hydrocarbon is transported from the reduction zone to the oxidation zone in adsorbed, partially oxidized form, which is clearly different from the known processes. The fact is, in these processes a separation of the hydrocarbon occurs at the end of the reduction zone. In accordance with the invention, the catalyst has a considerable load with hydrocarbon. In general, this load is at least 0.05 wt. % based on the weight of the catalyst.

Because of its good selectivity, the process according to the invention can be used with conventional catalysts, for instance as described in U.S. Pat. Nos. 4,371,702 and 4,632,916. In accordance with a preferred embodiment of the invention, the use of the above-described catalyst with a high surface area/volume ratio of the active phase on a support is highly attractive.

Such a catalyst can be obtained by providing the vanadium component with a valence of from 2.5 to 4.5 on the support, more particularly by homogeneously increasing the pH of a suspension of a suitable support in a solution of a vanadium salt in which the vanadium has an adjustable average valence which may vary between 2.5 and 4.5, and phosphate. This homogeneous adjustment of the pH can be effected in a number of ways. A first possibility is the injection of a compound such as urea under the surface of the well-stirred suspension. Another method is described in applicant's European patent application 225,659, by which method the active component is precipitated on the support in an electrochemical cell using an electrical current to be passed through the cell.

It is also possible to apply the vanadium component by impregnation of the support with a solution of a suitable vanadium salt, for instance vanadyl(IV)acetyl acetonate, whether or not in the presence of a phosphate component.

The preparation of the vanadium solution of lower valence preferably occurs by an electrochemical reduction of vanadium(V) in accordance with the prior art, as described in European patent application 223,299.

However, it is also possible to prepare the vanadium of lower valence in different ways in accordance with the current state of the art. Surprisingly, it has been found that in this way finely divided vanadium oxide/phosphate can be provided on supports such as titanium dioxide, zirconium oxide, aluminum oxide and silicon dioxide.

The phosphorus-oxygen component is preferably applied prior to, during or after the application of vanadium component. The application is preferably effected by means of a compound based on a phosphorus oxide, for instance one or more phosphates and/or a phosphorus-based acid.

Examples of suitable compounds are alkali metal and ammonium phosphates.

The catalyst obtained after calcination of the loaded support is highly wear-resistant and has a high active surface per unit weight. By virtue of this high specific surface of the active phase, the reaction with the saturated hydrocarbon can be carried out at temperatures as low as 300° C. or less while yet a high conversion per unit weight of catalyst is obtained. Accordingly, the process according to the invention will preferably be carried out with the above-described catalyst.

It is of great importance to control the transport of oxygen and the saturated organic compound in the catalyst bodies as well as possible. When a fixed catalyst bed is used, a catalyst with wide pores is required, since the allowable pressure drop across the catalyst bed disenables the use of small catalyst bodies (for instance less than 0.5 mm). Given the relatively large, minimum pore length in the catalyst bodies to be used, the pore diameter must be chosen to be relatively large. In a fluidized bed much smaller catalyst bodies, for instance of 100 μm, can be used. As a consequence, in fluidized bed catalysts narrower pores can be used. In accordance with the process according to the invention, the catalyst support can be selected such that, for specified dimensions of the catalyst bodies, the associated optimum pore diameter is obtained. With the current state of the art this is not possible with VPO catalysts.

Suitable supports preferably have a surface area between 1 and 400 $m^2/g$, determined by the BET method. Examples of suitable commercially available supports are:
a) Titanium dioxide, Engelhard 0602P, BET surface 100 $m^2/g$
b) Titanium dioxide of Degussa (P25) having a surface of 50 $m^2$ per gram. The titania support was also modified with a temperature treatment whereby the surface and the pore distribution were varied.
c) Silicon dioxide of Degussa (OX 50) having a surface of 50 $m^2$ per gram
d) Zirconium oxide, Daiichi 132-1, BET surface 40 $m^2/g$
e) Aluminum oxide of Degussa (C100) having a surface of 100 $m^2$ per gram, which may or may not have been priorly saturated with phosphate, in order to prevent absorption of the phosphate component by the support material during the preparation proper.
f) Silicon dioxide of Degussa (P 200) having a surface of 200 $m^2$ per gram.

The invention will now be further explained in and by a few examples, which should not be regarded as limitative.

EXAMPLES 1 AND 2

In accordance with the principle of the deposition precipitation from homogeneous solution on suspended supports, a few catalysts were prepared.

Vanadium(V) was electrochemically reduced in acid solutions of a pH<2 to vanadium having an initial valence of 3.7 on average. The phosphate to vanadium ratio was adjusted to 1.1:1 with a phosphate donor, for instance $NH_4H_2PO_4$. In a suspension of Degussa P25 (titanium dioxide with a surface of 50 $m^2$ per gram, which had been modified by a temperature treatment whereby the surface and the pore distribution were modified) the pH was homogeneously increased with exclusion of oxidizing components, such as oxygen from the air, by injecting a 1% solution of ammonia. The pH of the solution was 1.9 at the start and 7.0 at the end. Thus a titanium oxide-supported VPO catalyst with a load of 8.8 percent by weight, based on $(VO)_2P_2O_7$, was obtained. The dispersion number of the catalyst was 51.9. After testing, this number was determined again, which resulted in a value of 44.

The catalyst was tested, i.e. first the catalyst was loaded with butane (10% butane in argon, space velocity 2000 per hour) for 5 minutes in a fixed bed with 1.5 ml catalyst of a weight of 1.43 g (catalyst sieve fraction 0.09–0.15 mm) and subsequently, in a separate step, after flushing with argon at a space velocity of 4000 per hour, it was reoxidized for 2 minutes with a varying amount of oxygen (20 to 2% oxygen in argon, space velocity 2000 per hour). It can be seen in FIG. 1 that the selectivity to the desired product, being maleic acid anhydride, varies at the maximum amount of product stream between 40 and 50% for oxygen concentrations varying from 20 to 2%. The yield of products decreases with decreasing oxygen concentration, but the selectivity increases. The concentration of maleic acid anhydride (=54; maleic acid anhydride contains 4 C atoms, which means that the concentration of maleic acid anhydride corresponds with the carbon concentration/4) decreases with decreasing oxygen concentrations, but the concentrations of CO (=28) and $CO_2$ (=44) decrease more. The temperature at which the above-mentioned butane adsorption step was carried out was 273° C. The temperature at which the oxidation can be carried out and at which the loading can be carried out can, in principle, be adjusted independently when the gas streams are separated. However, this is not so easy with a fixed bed as described above. It was also found that the temperature rose (at least to 281° C.) in the reoxidation with oxygen. The amount of butane which was presented per amount of catalyst on the surface and was oxidized off it upon 20% $O_2$ for 2 minutes was 0.5 g/kg catalyst in the case of this catalyst under the above-mentioned conditions (10% butane for 5 minutes, at a temperature of 273° C.). The concentrations at which the catalyst bed was passed through continuously were 1.5% butane and 20% oxygen in argon at a space velocity of 2000 per hour. These are the flat portions between the peaks as shown in FIG. 1. The production increase upon the oxygen pulse after loading with butane can be clearly seen. Further, experiments have demonstrated that even when the catalyst is loaded again, a reasonable amount of maleic acid anhydride is produced. This amount represents a selectivity of 30% at a minimum and 60% at a maximum.

Figure 2:
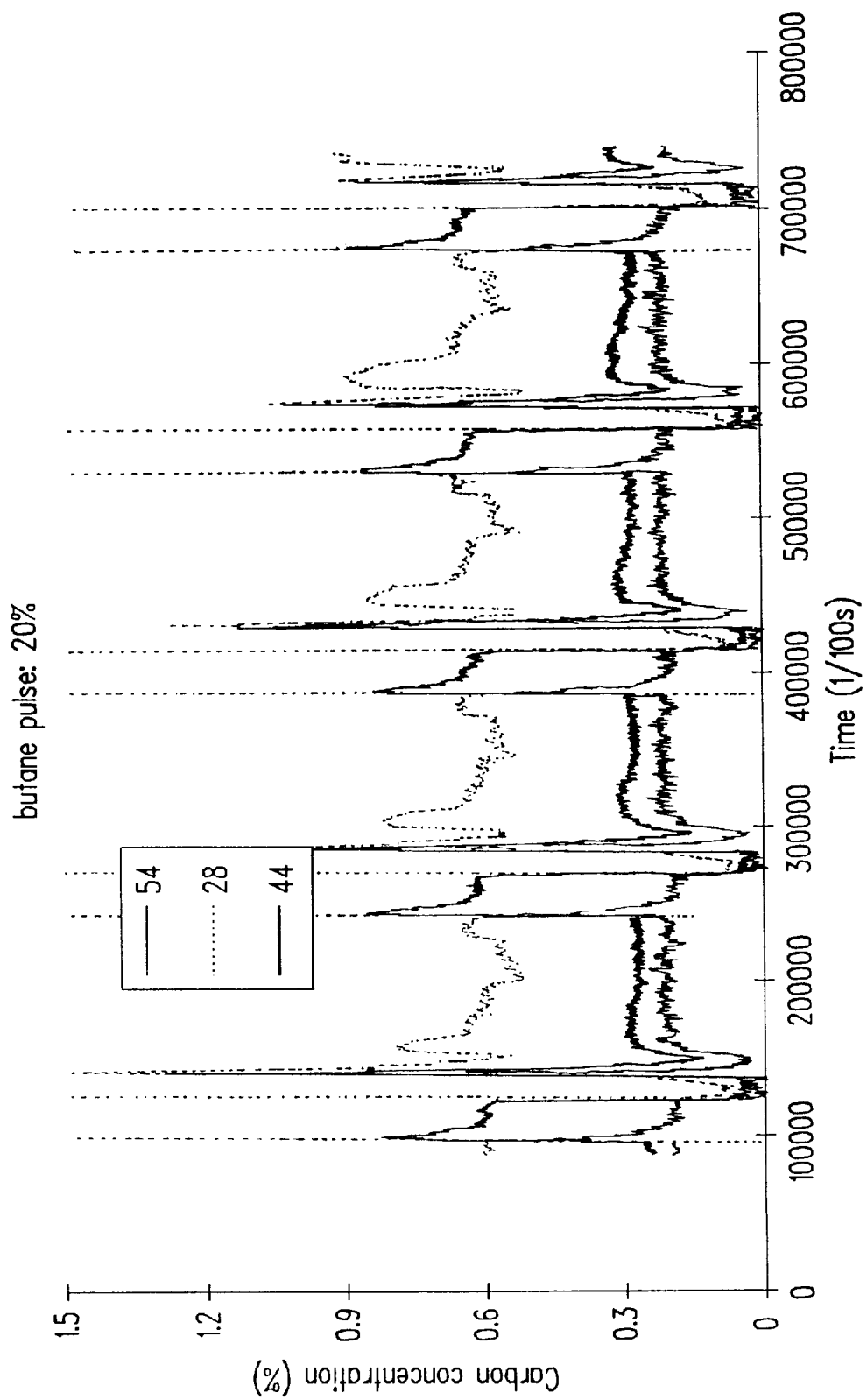
FIG. 2 is a further graph of carbon concentration versus time useful in explaining the invention.
Figure 3:
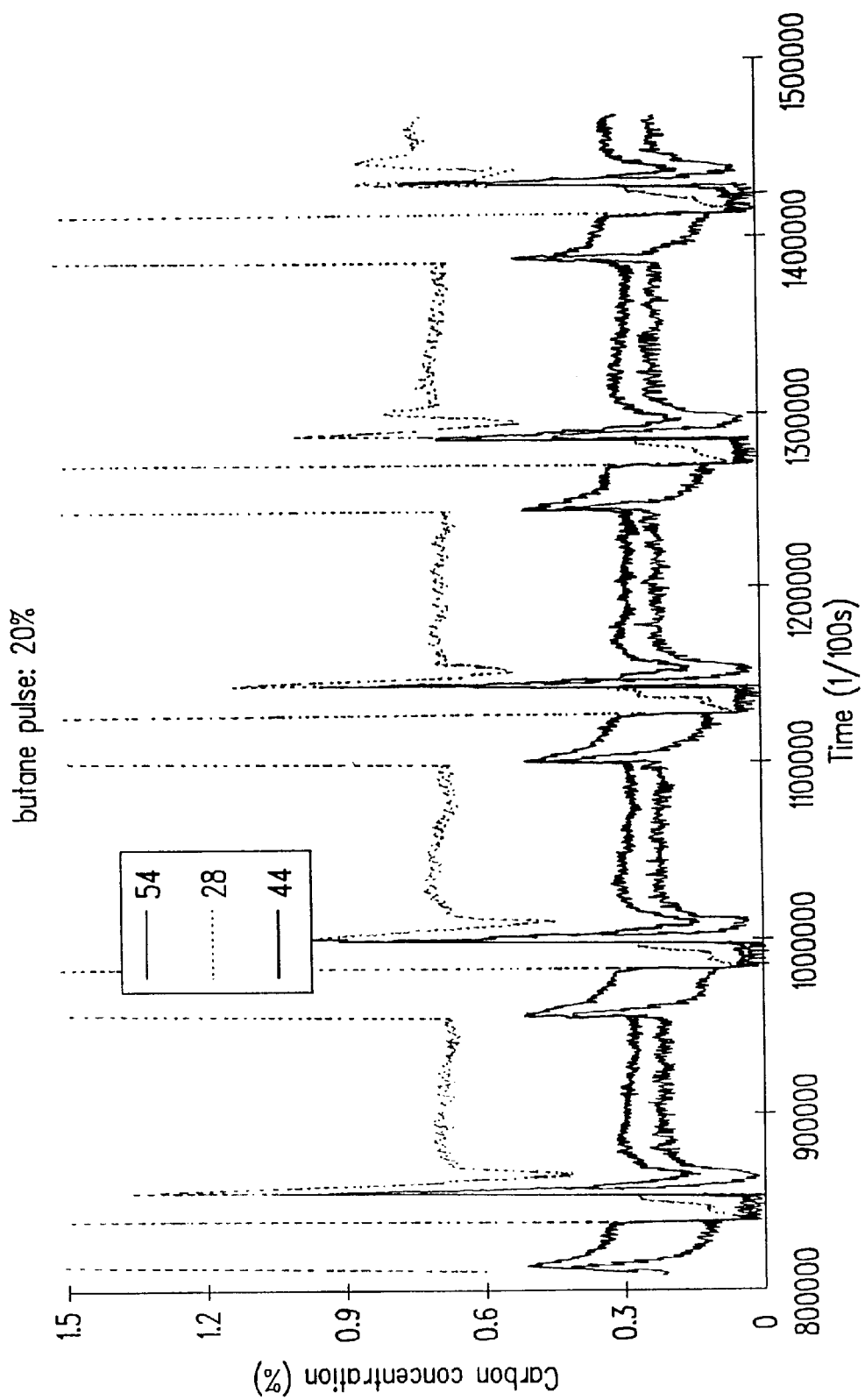
FIG. 3 is yet a further graph of carbon concentration versus time useful in explaining the invention.

A catalyst was prepared with an initial valence of vanadium of 2.9 on average and an adjusted phosphate to vanadium ratio of 1.1:1, supported on Degussa P25 with a load of 8.8 percent by weight, based on $(VO)_2P_2O_7$. The pH of the solution was 2.0 at the start and 7.0 at the end. The pH was increased by injecting a 1% solution of ammonia. The catalyst had a dispersion number of 52.8. The catalyst was tested, i.e. first the catalyst was loaded with butane (respectively, 20 and 10% butane in argon, space velocity 2500 per hour) for 5 minutes in a fixed bed with 1.2 ml catalyst of a weight of 1.2 g (catalyst sieve fraction 0.09–0.15 mm) and subsequently, in a separate step, after flushing with argon at a space velocity of 5000 per hour, it was reoxidized for 2 minutes with a varying amount of oxygen (20 to 4% oxygen in argon, space velocity 2500 per hour). It can be seen in FIGS. 2 and 3 that the selectivity to the desired product, being maleic acid anhydride, varies at the maximum amount of product stream between 33 and 40% for oxygen concentrations varying from 20 to 2%. The yield of products decreases with decreasing oxygen concentration, but the selectivity increases. The concentration of maleic acid anhydride (=54, maleic acid anhydride contains 4 C atoms, which means that the concentration of maleic acid anhydride corresponds with the carbon concentration/4) decreases with the decreasing oxygen concentrations, but the concentrations of CO (=28) and $CO_2$ (=44) decrease more. The total production of products in the case of loading with 20% butane is higher than in the case of 10% butane. However, the selectivity to the desired product, maleic acid anhydride, is slightly lower. The temperature at which the above-mentioned steps were carried out was 298° C. The concentrations at which the catalyst bed was continuously flown through were 1.5% butane and 20% oxygen in argon at a space velocity of 2500 per hour. These are the flat parts between the peaks shown in FIGS. 2 and 3. The production increase upon the oxygen pulse after loading with butane can be clearly seen. It was also found that the temperature rose (at least to 310° C.) in the reoxidation with oxygen. After testing, the catalyst had a dispersion number of 48.4.

As will appear clearly from the above-mentioned examples, the amount of butane which can be activated at the surface depends on the temperature at which the adsorption occurs and on the butane partial pressure to which the catalyst is exposed. The amount which can be oxidized off it again depends on the temperature at which the reoxidation occurs and at what oxygen partial pressure this occurs.

We claim:

1. A preparative process for the selective oxidation of an organic compound in the presence of a vanadium-phosphorus oxide catalyst, which process comprises a reduction phase and an oxidation phase, said preparative process comprising the steps of:

employing a fixed bed or a fluidized bed reactor, said reactor comprising a vanadium-phosphorus oxide catalyst;

passing through said reactor a feed stream comprising a hydrocarbon, wherein said hydrocarbon is contacted with said catalyst in the reduction phase of said process and in partially oxidized or non-oxidized form is adsorbed to the catalyst to form a loaded catalyst;

passing through said reactor an oxygen-containing gas, wherein the loaded catalyst is brought into the oxidation phase of said process and the desired product is formed in the presence of gaseous oxygen;

continuing to pass alternately through said reactor said feed stream comprising said hydrocarbon and said oxygen-containing gas; and isolating said desired product following each oxidation phase.

2. A process according to claim 1, wherein a fixed bed of vanadium-phosphorus oxide catalyst particles is used and alternately an oxygen-containing gas and a feed stream with hydrocarbon are passed through the bed.

3. A process according to claim 1, wherein maleic acid anhydride is prepared by oxidation of n-butane.

4. A process according to claim 1, wherein a catalyst on support is used, based on a metal oxide support.

5. A process according to claim 4 wherein the metal oxide support is selected from the group consisting of titanium oxide, zirconium oxide, silicon dioxide, aluminum oxide and combinations of two or more of these oxides.

6. A process according to claim 1, wherein an amount of hydrocarbon is supplied to the oxidation phase, in a minor proportion with regard to the amount of oxygen.

7. A process according to claim 1, wherein an amount of oxygen is supplied to the reduction phase, in a minor proportion with regard to the amount of hydrocarbon.

8. The process according to claim 1, wherein said catalyst is a heterogeneous vanadium-phosphorus oxide catalyst system comprising a support based on one or more metal oxides, said support having a surface, and vanadium-phosphorus oxide in an amount of from 0.01 to 45 wt. %, based on the weight of the catalyst and calculated as $(VO)_2P_2O_7$, wherein said vanadium-phosphorous oxide component is well-dispersed over said surface of said support, and wherein said catalyst has a dispersion number between 0.01 and 500, said catalyst having been made by a process that includes a step of applying the vanadium containing component to the surface of the catalyst support by homogeneously increasing the pH of a suspension of a suitable support in a solution of vanadium salt, in which the vanadium has an adjustable average valence which may vary between 2.5 and 4.5, phosphate being present before, during or after said step.

9. The process according to claim 8, wherein, in said catalyst system, said support is selected from the group consisting of titanium oxide, zirconium oxide, silicon dioxide, aluminum oxide and combinations of two or more of these oxides.

10. The process according to claim 8, wherein, in said catalyst system, said catalyst has been made by a process further including the steps of drying and calcining, to form a supported vanadium-phosphorus oxide catalyst.

11. The process of claim 8, wherein, in said catalyst system, said catalyst has a dispersion number between 0.01 and 300.

* * * * *

UNITED STATES PATENT AND TRADEMARK OFFICE
CERTIFICATE OF CORRECTION

PATENT NO. : 5,986,110
DATED : November 16, 1999
INVENTOR(S) : Geus et al.

It is certified that error appears in the above-indentified patent and that said Letters Patent is hereby corrected as shown below:

On the title page, item
[75] Inventors: John Wilhelm Geus, Bilthoven; Rudolf Alfred Overbeek, Utrecht, both of Netherlands Signed and Sealed this Twenty-seventh Day of March, 2001

*Attest:*

NICHOLAS P. GODICI

*Attesting Officer*     *Acting Director of the United States Patent and Trademark Office*